(12) United States Patent
Hohdatsu et al.

(10) Patent No.: US 8,394,581 B2
(45) Date of Patent: Mar. 12, 2013

(54) TEST METHOD ON FELINE VACCINATED WITH FELINE IMMUNODEFICIENCY VIRUS VACCINE, AND ANTIGEN FOR USE IN THE TEST

(75) Inventors: Tsutomu Hohdatsu, Aomori (JP); Kenji Motokawa, Saitama (JP); Hajime Kusuhara, Saitama (JP)

(73) Assignee: The Kitasato Institute (JP)

( * ) Notice: Subject to any disclaimer, the term of this patent is extended or adjusted under 35 U.S.C. 154(b) by 114 days.

(21) Appl. No.: 12/670,592

(22) PCT Filed: Jul. 25, 2008

(86) PCT No.: PCT/JP2008/063383
§ 371 (c)(1),
(2), (4) Date: May 17, 2010

(87) PCT Pub. No.: WO2009/014207
PCT Pub. Date: Jan. 29, 2009

(65) Prior Publication Data
US 2010/0267047 A1    Oct. 21, 2010

(30) Foreign Application Priority Data
Jul. 25, 2007  (JP) .................................. 2007-192975

(51) Int. Cl.
*C12Q 1/70*    (2006.01)
*A61K 39/21*   (2006.01)
(52) U.S. Cl. ......................................... 435/5; 424/208.1
(58) Field of Classification Search .......................... None
See application file for complete search history.

(56) References Cited

U.S. PATENT DOCUMENTS

| 5,846,825 | A | 12/1998 | Yamamoto | |
|---|---|---|---|---|
| 6,447,993 | B1 | 9/2002 | Yamamoto | |
| 6,461,616 | B1 * | 10/2002 | Montelaro et al. | 424/205.1 |
| 6,727,078 | B2 * | 4/2004 | Montelaro et al. | 435/69.1 |
| 2003/0026814 | A1 * | 2/2003 | Montelaro et al. | 424/208.1 |

FOREIGN PATENT DOCUMENTS

| EP | 1709447 | 6/2009 |
|---|---|---|
| JP | 7159408 | 6/1995 |
| JP | 11513031 | 11/1999 |
| JP | 2007514753 | 6/2007 |
| WO | 2006011917 | 2/2006 |

OTHER PUBLICATIONS

Kusuhara et al., "Dual-subtype vaccine (Fel-O-Vax FIV) protects cats against contact challenge with heterologous subtype B FIV infected cats", Veterinary Microbiology, 2005, 108:155-165.

Yamamoto et al., "Development of IL-2-Independent Feline Lymphoid Cell Lines Chronically Infected with Feline Immunodeficiency Virus: Importance for Diagnostic Reagents and Vaccines", Intervirology, 1991, 32:361-375.

Fontenot et al., "Evaluation of Feline Immunodeficiency Virus and Feline Leukemia Virus Transmembrane Peptides for Serological Diagnosis", Journal of Clinical Microbiology, Jul. 1992, 30(7):1885-1890.

Hohdatsu, "Current Situation and Clinical Application of the FIV Vaccine", English Translation, Mar. 2006, 1:159.

Hohdatsu et al., "Effect of dual-subtype vaccine against feline immunodeficiency virus infection", Veterinary Microbiology, 1997, 58:155-165.

Kusuhara et al., "Serological differentiation of FIV-infected cats from cats vaccinated with the Dual-Subtype Feline immunodeficiency virus (FIV) inactivated vaccine (Fel-O-Vax FIV)", English Translation, Aug. 2005, 31:110.

Kusuhara et al., "Serological differentiation of FIV-infected cats from dual-subtype feline immunodeficiency virus vaccine (Fel-O-Vax FIV) inoculated cats", Veterinary Microbiology, 2007, 120:217-225.

Merza et al., "Immunoaffinity purification of two major proteins of bovine leukemia virus (gp51 and p24) and their use for discrimination between vaccinated and infected animals", Journal of Virological Methods, 1991, 22:345-353.

Murray, "Identifying FIV Vaccinates", Journal of the American Veterinary Medical Association, Letters to the Editor, Mar. 15, 2003, 222(6):710.

Pu et al., "Dual-subtype FIV vaccine protects cats against in vivo swarms of both homologous and heterologous subtype FIV isolates", AIDS, 2001, 15:1225-1237.

Rovinski et al., "Engineering of Noninfectious HIV-1-like Particles Containing Mutant gp41 Glycoproteins as Vaccine Candidates That Allow Vaccinees to Be Distinguished from HIV-1 Infectees", Virology, 1999, 257:438-448.

Uhl et al., "FIV vaccine development and its importance to veterinary and human medicine: a review FIV vaccine 2002 update and review", Veterinary Immunology and Immunopathology, 2002, 90:113-132.

International Search Report for PCT/JP2008/063383 dated Sep. 25, 2008.

Written Opinion for PCT/JP2008/063383 dated Sep. 25, 2008.

* cited by examiner

*Primary Examiner* — Bao Li
(74) *Attorney, Agent, or Firm* — Andrus, Sceales, Starke & Sawall, LLP (57) ABSTRACT

Since FIV-vaccinated cats produce antibodies against FIV, distinguishing them from FIV-infected cats is difficult by serological diagnostic methods using FIV and FIV-derived substances. The present invention enables tests for determining the presence or absence of a FIV vaccination history in a cat by detecting antibodies that are produced as a result of vaccination of a cat with an FIV vaccine, but not as a result of FIV infection. Using the methods of the present invention, whether an anti-FIV antibody-positive cat is infected with FIV or has been vaccinated can be conveniently distinguished.

10 Claims, 4 Drawing Sheets

TEST METHOD ON FELINE VACCINATED WITH FELINE IMMUNODEFICIENCY VIRUS VACCINE, AND ANTIGEN FOR USE IN THE TEST

CROSS-REFERENCE TO RELATED APPLICATIONS

The present application is the U.S. National Stage of International Application No. PCT/JP2008/063383, filed on Jul. 25, 2008, and published in the Japanese language on Jan. 29, 2009, and which claims the benefit under 35 U.S.C. §119 to Japanese Application No. JP 2007-192975, filed on Jul. 25, 2007.

TECHNICAL FIELD

The present invention relates to methods for serologically distinguishing whether a cat is positive for anti-feline immunodeficiency virus (FIV) antibody due to FIV infection or due to vaccination with an FIV vaccine.

BACKGROUND ART

FIV infection has been attracting attention as one of the most important infectious diseases in the area of small animal veterinary medicine, and also as an animal model for human immunodeficiency virus infection. Since the discovery of FIV in 1986, studies on FIV vaccines were conducted worldwide, but vaccine development proved to be difficult as FIV has multiple subtypes. Dr. Yamamoto of the United States successfully developed a highly effective vaccine by combining multiple subtypes, which was named the multi-subtype vaccine (Non-patent Document 1). Use of the FIV Shizuoka strain, which was discovered in a collaborative research between Kitasato University and the Kitasato Research Institute, as the antigen for this multi-subtype vaccine was effective for increasing the efficacy (Non-patent Document 2). This multi-subtype vaccine containing the FIV Shizuoka strain was marketed in 2002 by Fort Dodge Animal Health of the U.S. (Product name; Fel-O-Vax FIV). This vaccine drew attention as the world's first lentivirus vaccine.

However, vaccination with this FIV vaccine led a new problem concerning diagnostic methods for FIV infection. The issue concerns how to distinguish FIV-infected cats from FIV-vaccinated cats. Until then, FIV infection was diagnosed by detecting anti-FIV antibodies. Diagnostic agents for detecting anti-FIV antibodies are commercially available from several companies, and are commonly used for clinical diagnoses. However, cats vaccinated with the FIV vaccine would also be judged positive with these diagnostic agents as such cats will also produce anti-FIV antibodies. That is, with the current diagnostic agents, both FIV-infected cats and FIV-vaccinated cats will be deemed positive, and it cannot be distinguished whether an anti-FIV antibody-positive cat is actually an FIC-infected cat. As a result, FIV vaccination relatively decreases the significance of such serological tests. This issue has become a limiting factor for the widespread use of the FIV vaccine.

As a method for diagnosing FIV infection, test methods for detecting viruses are also available. Test methods for detecting viruses do not depend on the presence or absence of antibodies; therefore, they allow correct diagnosis independently of vaccination. Generally-used, practical methods for detecting viruses are gene amplification methods represented by the PCR method. Since the PCR method is a sensitive and highly specific method, its diagnostic significance is high, and is an effective test method when a diagnosis cannot be confirmed by a serological test method. However, since special materials and equipments are necessary for these gene amplification methods, they are not suitable for use in clinical practice. Consequently, convenient test methods for distinguishing FIV infection and FIV vaccination that can also be used in clinically are required.

[Non-patent Document 1] Pu R, Coleman J, Omori M, Arai M, Hohdatsu T, Huang C, Tanabe T, Yamamoto J K., Dual-subtype FIV vaccine protects cats against in vivo swarms of both homologous and heterologous subtype FIV isolates. (2001) AIDS 15 (10): 1225-1237.

[Non-patent Document 2] Hohdatsu T, Okada S, Motokawa K, Aizawa C, Yamamoto J K, Koyama H., Effect of dual-subtype vaccine against feline immunodeficiency virus infection. (1997) Vet. Microbiol. 58 (2-4): 155-165

DISCLOSURE OF THE INVENTION

Problems to be Solved by the Invention

An objective of the present invention is to provide methods for serologically distinguishing whether a cat is anti-feline immunodeficiency virus (FIV) antibody-positive due to FIV infection or due to vaccination with an FIV vaccine.

Means for Solving the Problems

The present inventors aimed at developing test methods for distinguishing FIV-infected cats from FIV-vaccinated cats by serological means.

FIV propagates in primary-cultured feline lymphocytes, FeT-J cells and Kumi-1 cells which are feline lymphocyte-derived cell lines, CRFK cells derived from feline kidney, and such. Many of the experimental vaccines tested so far were produced using virus particles or partial proteins thereof from virus propagated in cultured cells (Uhl, E. W., Heaton-Jones, T. G., Pu, R. and Yamamoto, J. K., 2002. FIV vaccine development and its importance to veterinary and human medicine: a review FIV vaccine 2002 update and review. Vet. Immunol. Immunopathol. 90, 113-132). Of these, a vaccine produced by inactivating FIV-infected culture cells by formalin treatment and then using it as is as the vaccine antigen showed a high efficacy.

Antigens produced by propagating viruses in cultured cells often include culture cell components. Therefore, the present inventors suspected that cats immunized with vaccines produced by propagating FIV in cultured cells, inactivating these cells as a whole and using these as antigen, may produce antibodies against the cellular components included in the vaccine. On the other hand, antibodies against such cultured cells are not produced by natural FIV infection. Accordingly, experiments were performed to see whether only the FIV-vaccinated cats can be identified by detecting antibodies against cellular components derived from cultured cells.

First, whether the sera from FIV-vaccinated cats react with cellular components was confirmed using the ELISA (Enzyme-Linked Immunosorbent Assay) method. Since FIV propagated best in feline lymphocyte-derived cells, solubilized FeT-J cells derived from feline lymphocytes were used as the antigens for ELISA. As a result, the sera from FIV-vaccinated cats strongly reacted to cellular components of FeT-J cells. On the other hand, the sera from FIV-infected cats hardly reacted to these antigens (see Example 1). When producing inactivated vaccines, the virus is generally inactivated by formalin treatment. Therefore, reactivity was also confirmed for ELISA antigens of FeT-J cells subjected to formalin treatment. As a result, it was confirmed that formalin-treated cellular components increased reactivity to the vaccinated cat sera (see Example 1). Furthermore, to confirm whether the antibodies against cellular components are produced specifically in cats vaccinated with the FIV vaccine, the reactivity to the cellular components of FeT-J cells was tested for the sera from cats immunized with a vaccine for cats (including vaccines against feline panleukopenia virus, feline calicivirus, feline infectious rhinotracheitis virus, feline leukemia virus, or such) which does not contain FIV. As a result, the sera from cats vaccinated with a vaccine for cats that does not contain FIV, hardly reacted to the cellular components of FeT-J cells (see Example 2). Accordingly, this confirmed that FIV-vaccinated cats and FIV-infected cats can be distinguished by using cellular components derived from FeT-J cells as diagnostic antigens.

Next, to confirm whether such reactions can be observed in cell lines other than FeT-J cells, the reactivity of FIV-vaccinated cat serum to cellular components of various cultured cells was checked. As a result, as with FeT-J cells, antigens for ELISA produced from any of the feline lymphocyte-derived 3201 cells, the feline kidney-derived CRFK cells, and the feline fetus-derived fcwf-4 cells showed high reactivity with the sera from FIV-vaccinated cats and did not react with the sera from FIV-infected cats. In addition, similar reactions were verified with simian kidney-derived Vero cells. Therefore, it was confirmed that the reactivity does not depend on the animal species or the tissue from which the cells originate, and is not limited to particular cell lines (see Example 3).

To identify which culture cell constituent(s) the antibodies against cellular components produced by FIV vaccine-vaccinated cats reacted to, FeT-J cells were solubilized, fractionated into cytoplasm, cell membrane, cell nucleus, and cytoskeleton, and the reactivities of feline sera with each of the fractions were ascertained using the ELISA method. As a result, it was verified that antibodies against all of cytoplasm, cell membrane, cell nucleus, and cytoskeleton were produced in cats vaccinated with the FIV vaccine (see Example 4). Therefore, this indicated that when determining the reactivity to feline serum using a certain fraction of cellular constituents, those cellular constituents may be any of the cytoplasm, cell membrane, cell nucleus, and cytoskeleton. Among them, higher responses were observed from the cell membrane and cytoskeleton.

Specificity of the response of the FIV-vaccinated cat serum to the cellular components of cultured cells was confirmed using a dot blot method. The cellular components of FeT-J cells homogenized by ultrasonication were adsorbed onto a nitrocellulose membrane, this was reacted with FIV-vaccinated cat serum, FIV-infected cat serum, and SPF cat serum, and their responses were observed. At that time, a synthetic peptide of the immunodominant domain of a transmembrane protein (TM peptide) which is a structural protein of FIV useful for diagnosis of FIV infection was similarly adsorbed onto a nitrocellulose membrane, and the responses were observed. As a result, the sera from FIV-infected cats reacted to the TM peptide, but did not react to the cellular components. On the other hand, the sera from vaccinated cats reacted to both the TM peptide and the cellular components. Furthermore, SPF cat sera did not react to either one (see Example 5). Therefore, the dot blot method also showed that cellular components react specifically with FIV-vaccinated cat serum.

Furthermore, whether the presence or absence of vaccination with an FIV vaccine can be confirmed was assessed by using a conventional immunochromatography method using a commercially available simple serodiagnostic agent. FIV-vaccinated cat serum, FIV-infected cat serum, and SPF cat serum were reacted with an immunochromatography membrane to which cellular components of the FeT-J cell have been adsorbed. When a colloidal gold-labeled anti-feline IgG antibody was subsequently reacted with this, only the serum of FIV-vaccinated cat reacted to the cellular components, and no reaction was observed with the FIV-infected cat serum and the SPF cat serum (see Example 6).

These experiment results showed that FIV-infected cats and FIV-vaccinated cats can be distinguished by serological test methods using such antigens.

As described above, the present inventors succeeded in developing a novel method that allows testing for the presence or absence of a FIV vaccination history in a cat, for example by using as an index the presence or absence of antibodies against constituents of cells used for FIV culture during FIV vaccine production.

More specifically, the present invention was completed by developing a method for testing the presence or absence of a FIV vaccination history in a cat by detecting antibodies that are produced as a result of vaccination with an FIV vaccine, but not as a result of FIV infection.

The present invention relates to methods for serologically distinguishing whether a cat is anti-feline immunodeficiency virus (FIV) antibody-positive due to FIV infection or due to vaccination with an FIV vaccine, more specifically, the present invention provides:

[1] a method for testing the presence or absence of a FIV vaccination history in a cat, wherein the test method detects an antibody which is produced as a result of vaccination with an FIV vaccine but not as a result of FIV infection;

[2] the test method of [1], wherein a feline subject is determined to have a FIV vaccination history when the antibody is detected by an antigen-antibody reaction method;

[3] the test method of [2], wherein a substance which may cause production of an antibody by inoculation into a cat, is used as antigen in the antigen-antibody reaction method;

[4] the test method of [3], wherein the substance is a substance included in an FIV vaccine but excluding FIV and FIV-derived substances;

[5] the test method of [3], wherein the substance is a substance constituting a cell;

[6] the test method of [5], wherein the substance constituting a cell is a cell membrane, cytoplasm, nucleus, or cytoskeleton;

[7] the test method of [5] or [6], wherein the cell is a feline-derived cell;

[8] the test method of [5] or [6], wherein the cell is a cell derived from a non-feline animal;

[9] the test method of any one of [1] to [8], wherein serum, plasma, or whole blood derived from a feline subject is used as a test sample;

[10] an agent for testing an FIV-vaccinated cat, comprising as an active ingredient a substance used as an antigen in the test method of any one of [1] to [9];

[11] the agent for testing an FIV-vaccinated cat of [10], wherein the substance is a substance constituting a cell;

[12] the agent for testing an FIV-vaccinated cat of [11], wherein the substance constituting a cell is a cell membrane, cytoplasm, nucleus, or cytoskeleton;

[13] the agent for testing an FIV-vaccinated cat of [12], wherein the cell is a feline-derived cell; and

[14] the agent for testing an FIV-vaccinated cat of [12], wherein the cell is a cell derived from a non-feline animal.

The present invention also provides below:

[15] a method for testing the presence or absence of a FIV vaccination history in a cat, comprising the step of detecting an antibody produced as a result of vaccination with an FIV vaccine but not as a result of FIV infection, wherein a feline subject is determined to have a FIV vaccination history when the aforementioned antibody is detected and a feline subject is determined not to have a FIV vaccination history when the aforementioned antibody is not detected by an antigen-antibody reaction method; and

[16] use of a substance used as an antigen in the test method of any one of [1] to [9] in producing a test agent for cats vaccinated with an FIV vaccine.

MODE FOR CARRYING OUT THE INVENTION

The present invention provides methods for testing the presence or absence of a FIV vaccination history in a cat. A preferred embodiment of the test methods of the present invention is a method having the characteristic of detecting antibodies produced as a result of vaccination of a cat with an FIV vaccine, but not as a result of FIV infection.

The test method of the present invention is a method for determining that a feline subject has a FIV vaccination history when the aforementioned antibodies are detected.

The antibodies can usually be detected by an antigen-antibody reaction method. Those skilled in the art can easily evaluate the presence or absence of desired antibodies in a test sample by an antigen-antibody reaction method. The antigen-antibody reaction method can be suitably performed by generally known techniques which specifically include ELISA, fluorescent antibody method, immunochromatography, Western blotting, dot blotting, immunoprecipitation, and agglutination.

In the above-mentioned antigen-antibody reaction methods of the present invention, suitable examples of antigens that can be used for antibody detection include substances that may lead to production of antibodies by vaccination in cats (herein, they may be referred to as "detection antigens of the present invention").

Preferred embodiment of the detection antigens of the present invention includes, for example, substances that are not FIV, FIV-derived substances, or substances produced based on the genetic information of FIV that are included in the vaccine, substances that may cause production of antibodies against those substances in vaccinated animals.

More specifically, a preferred embodiment of the present invention includes, for example, test methods using as antigens in the aforementioned antigen-antibody reaction methods, substances included in an FIV vaccine (except for FIV or FIV-derived substances), which are substances that may cause production of antibodies by vaccination in cats.

As the present invention's antigens used for testing, one may use, for example, substances derived from cultured cells (cellular constituents) used for FIV propagation when producing a vaccine. In this case, cells are desirably under FIV-uninfected conditions, but even if they are under infected conditions, they can be used by fractionating the necessary antigens.

More specifically, a preferred embodiment of the present invention is a test method characterized by the use of constituents (cell-derived substances) of cells used in FIV culture for an FIV vaccine production as antigens in the aforementioned antigen-antibody reaction methods.

The aforementioned cells of the present invention are preferably cells derived from cats. For example, substances derived from feline lymphocyte-derived cells can be used. Specifically, primary-cultured feline lymphocytes, feline lymphocyte-derived interleukin 2-dependent subcultured cells, subcultured 3201 cells, subcultured FeT-J cells (ATCC number CRL-11967), or such may be used.

In addition to substances deriving from lymphocyte-derived cells, those from other tissue-derived cells may also be used as substances derived from cells. Specifically, CRFK cells derived from a feline kidney, fcwf-4 cells derived from a feline fetus, or such may be used. Besides cat-derived cells, substances derived from cells of other species may also be used. In this case, as with cat-derived cells, they may be lymphocyte-derived cells, or cells derived from other tissues. Specifically, Vero cells derived from a simian kidney, or such may be used. Such cells may be cells immediately after separation from a living body, primary cultured cells, continuous cell lines, or such cells with molecular-biological modifications.

Furthermore, cells from which the present invention's antigens used for testing derive may be cells that are used in FIV culture for an FIV vaccine production, or cells that are different from the cells used for vaccine production.

An example includes an embodiment in which the cells used for vaccine production are feline cells, and feline cells different to those used for vaccine production are used as the present invention's antigens used for testing. A further example is an embodiment that uses non-feline cells as the present invention's antigens used for testing when using feline cells for vaccine production. These embodiments are included in the present invention.

When using substances derived from these cells as antigens, they can be easily handled as antigens by solubilizing the cells. Specifically, antigens solubilized using surfactants such as Triton X-100 or NONIDET P-40 are suitable for use in various assay systems. Furthermore, by homogenizing the cells by ultrasonication, antigens similar to those obtained by solubilization using a surfactant can be obtained without the use of a surfactant.

Cells degraded by solubilization, homogenization by ultrasonication, or other chemical or physical methods can be used as they are, or a certain component can be fractioned and/or purified by methods such as density gradient centrifugation, ultrafiltration, various types of chromatographies, or gel filtration and used as antigens for diagnosis. In this case, among the cellular components, any of the cell membrane, cytoplasm, nucleus, and cytoskeleton, may be used. Preferably, cell membrane or cytoskeleton may be used as antigens used for testing.

These antigens can be treated by formalin fixation. Fixation increases the stability of the antigens, and the reactivity can also be increased at the same time. For this fixation, one may use, in addition to formalin, formaldehyde, paraformaldehyde, glutaraldehyde, and such, and also various reagents for chemically denaturing and/or fixing proteins. Furthermore, physicochemical treatment methods such as γ-ray irradiation or heat treatment can be used.

In addition, as antigens for this purpose, also usable are substances derived from even cultured cells other than those used for vaccine production.

Antigens used for testing do not have to be substances derived from cultured cells. As long as the substances are not FIV, FIV-derived substances, and substances produced based on the genetic information of FIV that are included in the vaccine, can be used as antigens as long as they can cause production of antibodies against them in animals vaccinated with the vaccine. They may be stabilizers or adjuvants added to the vaccine. Gelatin or albumin is generally used as stabilizer. Generally, cholera toxin, hemolysin-like protein, or Freund's adjuvant are used as adjuvant.

Furthermore, antigens used for testing need not be substances derived from the vaccine production process. For example, proteins, peptides, or such that do not react with ordinary animal sera, which have antigenicity, may be added to the vaccine. Vaccines subjected to some kind of modification to facilitate differentiation between immunization by vaccines and naturally-occurring infection are sometimes called marker vaccines. Such vaccines comprising an exogenous protein/peptide or such having antigenicity are also called exogenous positive marker vaccines, and such substances are called exogenous positive markers.

As specific examples of present invention's antigens used for testing, which are not derived from the vaccine production process, exogenous positive markers that suit the following conditions can be used:
1. substances not present in the breeding environment of cats, or substances with no possibility or very low possibility of exposure to cats;
2. substances not present in vaccines or pharmaceuticals used for cats;
3. substances that do not react with the serum of ordinary (preimmunized) cats;
4. substances having antigenicity; and
5. substances that are harmless (have low toxicity) to cats.

As a specific example of an exogenous positive marker, there is a report on a mycoplasma vaccine for pigs (Blending of a conventional *Mycoplasma hyopneumoniae* vaccine with a positive marker: tracking of immunized pigs by peptide-specific antibodies raised to the marker component, B. Walders et al./Research in Veterinary Science 78 (2005) 135-141). In this report, a structure produced by chemically linking a peptide comprising 13 residues of D-amino acids (non-natural form) and Keyhole Limpet Hemocyanin (KLH) was used as the marker, and pigs immunized with this structure produced very strong anti-peptide antibodies. Furthermore, this structure is not present in the breeding environment of the pigs nor in commercially available vaccines for pigs, and non-immunized pig serum did not react with this structure. Therefore, in the present invention, a specific example of substances not derived from the vaccine production process includes a peptide comprising non-natural D-amino acids. Further examples include structural proteins of pathogens that do not infect cats, which are antigenic proteins or peptides specific to that pathogen (for example, partial proteins of the bovine papillomavirus).

Since vaccinated animals produce antibodies against these proteins or peptides, they can be tested for the presence or absence of a vaccination history.

By using the method of the present invention, FIV-infected cats and FIV-vaccinated cats can be distinguished (identified). This differentiation method can be carried out suitably by combined use of the existing method for diagnosing FIV-infected cats (test method for detecting anti-FIV antibodies) and the test method of the present invention. More specifically, when a feline subject shows a positive result for an existing diagnostic method for FIV-infected cats (anti-FIV antibody-positive), and additionally shows a negative result for the test method of the present invention, that feline subject is determined to be infected with FIV.

An embodiment which combines an existing diagnostic method for FIV-infected cats and a method of the present invention for determining the presence or absence of FIV infection are also included in the present invention, so long as it uses a method of the present invention.

Samples subjected to the methods of the present invention are ordinarily samples derived from feline subjects, and preferably, serum, plasma, or whole blood (anticoagulated blood) derived from feline subjects is used as sample.

The present invention provides antigens for distinguishing FIV-infected cats from FIV-vaccinated cats by serological test methods. The antigens are useful as test agents to be used in the test methods of the present invention. More specifically, the present invention provides agents to test for FIV-vaccinated cats (herein, they may be described as "test agents of the present invention") comprising as the active ingredient a substance used as an antigen in the test method of the present invention.

In the test agent of the present invention, examples of the aforementioned substances include cell-constituting substances. The cell-constituting substances specifically include cell membrane, cytoplasm, nucleus, or cytoskeleton. Furthermore, the cells are preferably cells derived from cats, but they may be cells derived from non-feline animals.

Antigens which are components of the test agents of the present invention are preferably used as reagents (antigens for detection) for the antigen-antibody reaction method in the test methods of the present invention. The method of detecting a desired antibody using antigens is a common technique, and those skilled in the art can perform the method without particular difficulty.

All prior art references cited herein are incorporated by reference into this description.

EXAMPLES

Herein below, the present invention will be specifically described with reference the Examples, but it is not to be construed being limited thereto.

Example 1

Reactivity of FIV-Infected Cat Serum and FIV-Vaccinated Cat Serum to Cellular Components

[Materials and Methods]

FeT-J cells cultured in RPMI1640 medium were washed twice with phosphate-buffered saline (PBS⁻) and then resuspended in PBS⁻ to bring the cell count to approximately $2.0 \times 10^7$/mL. TritonX-100 was added to this cell suspension solution to a final concentration of 0.05%, and this was slowly stirred at 4° C. for one hour to dissolve the cells. A part of this was centrifuged at 20,000×g for 10 minutes, and the collected supernatant was filtered through a 0.2-µm filter to give formalin-untreated antigens. Formalin was added to the residual to a final concentration of 0.3%, and formalin treatment (fixation) was carried out by stirring at room temperature for 36 hours or more. This was centrifuged for ten minutes at 20,000×g, and the collected supernatant was filtered through a 0.2-µm filter to give formalin-treated antigens.

As samples, the sera from twelve SPF cats vaccinated with the FIV vaccine three times at three-week intervals (FIV-vaccinated group) and the sera from six FIV-infected SPF cats (FIV-infected group) were used.

The formalin-untreated antigens and the formalin-treated antigens were individually diluted with a coating buffer, dispensed into a 96-well ELISA plate in 100-µL aliquots, and were left to stand at 4° C. overnight for coating of the wells with antigens. Each serum was diluted at 1:100 individually with a serum diluent, added in 100-µL aliquots to the antigen-coated plate washed with a washing solution, and then reacted at 37° C. for one hour. The plate was washed with the washing solution, then POD-labeled anti-feline IgG goat serum was added in 100-µL aliquots, and then this was reacted at 37° C. for 30 minutes. The plate was washed with the washing solution, then TMB substrate solution was added in 100-µL aliquots, and this was reacted at room temperature for 20 minutes, and then a stop solution was added in 100-µL aliquots to stop color development, and then the absorbance (O.D. value) at 450 nm was measured.

[Results and Discussion]

All sera in the FIV-vaccinated group strongly reacted to ELISA antigens prepared from FeT-J cells. In this case, performing formalin treatment on the antigens was confirmed to increase the reactivity to the sera of the FIV-vaccinated group by 1.9- to 5.6-fold according to O.D. value ratios (Table 1). On the other hand, the sera of FIV-infected group hardly showed any reaction to formalin-untreated antigens as well as formalin-treated antigens (Table 1).

TABLE 1

| GROUP | CAT NUMBER | REACTIVITY TO CELLULAR COMPONENT (OD VALUE) | | OD VALUE RATIO* |
|---|---|---|---|---|
| | | FORMALIN TREATMENT | NO FORMALIN TREATMENT | |
| FIV VACCI-NATED GROUP | ACU2 | 2.583 | 1.261 | 2.0 |
| | QCQ3 | 1.771 | 0.648 | 2.7 |
| | QCQ2 | 1.766 | 0.495 | 3.6 |
| | ACZ4 | 2.338 | 0.793 | 2.9 |
| | QCT2 | 2.887 | 1.521 | 1.9 |
| | ACV5 | 2.197 | 0.952 | 2.3 |
| | ACY3 | 1.832 | 0.800 | 2.3 |
| | QCI1 | 1.860 | 0.456 | 4.1 |
| | ACX6 | 2.444 | 0.816 | 3.0 |
| | QCO4 | 1.878 | 0.335 | 5.6 |
| | AAA1 | 0.998 | 0.257 | 3.9 |
| | AAD4 | 1.341 | 0.416 | 3.2 |
| FIV INFECTED GROUP | 292 | 0.031 | 0.145 | 0.2 |
| | 1E | 0.010 | 0.075 | 0.1 |
| | 6E | 0.013 | 0.091 | 0.1 |
| | 1F | 0.028 | 0.081 | 0.3 |
| | 6F | 0.061 | 0.108 | 0.6 |
| | 7F | 0.094 | 0.103 | 0.9 |

*O.D. value on formalin-treated antigen/O.D. value on formalin-untreated antigen Therefore, cellular components derived from FeT-J cells are useful as diagnostic antigens for detecting cats vaccinated with the FIV vaccine, and it was also shown that the use of formalin-treated antigens can yield high reactivity.

Example 2

Specificity of the Reaction of FIV-Vaccinated Cat Serum to Cellular Components

[Materials and Methods]

Twelve SPF cats were vaccinated with a commercially available feline 3-way vaccine (against feline panleukopenia virus, feline calicivirus, and feline infectious rhinotracheitis virus) and were classified as the 3-way-vaccinated group. Four SPF cats were vaccinated with the commercially available feline leukemia vaccine and were classified as the feline leukemia-vaccinated group. Four SPF cats were vaccinated with both the feline 3-way vaccine and the feline leukemia vaccine to be classified as the feline 3-way+feline leukemia-vaccinated group. For all of these vaccines, vaccination was carried out twice at a two-week interval, and the sera collected two weeks after the second vaccination were used as the samples. For the FIV-vaccinated group, 14 SPF cats were vaccinated with the FIV vaccine three times at three-week intervals, and the sera collected three weeks after the third vaccination were used as the samples.

As the antigens for ELISA, the formalin-treated antigens prepared in Example 1 were used. Reactions were carried out as described in Example 1, and the reaction of each sera to the cellular components were measured. Instead, OPD substrate solution was used for the color developing solution, and the absorbance was measured at 492 nm.

[Results and Discussion]

Figure 1:
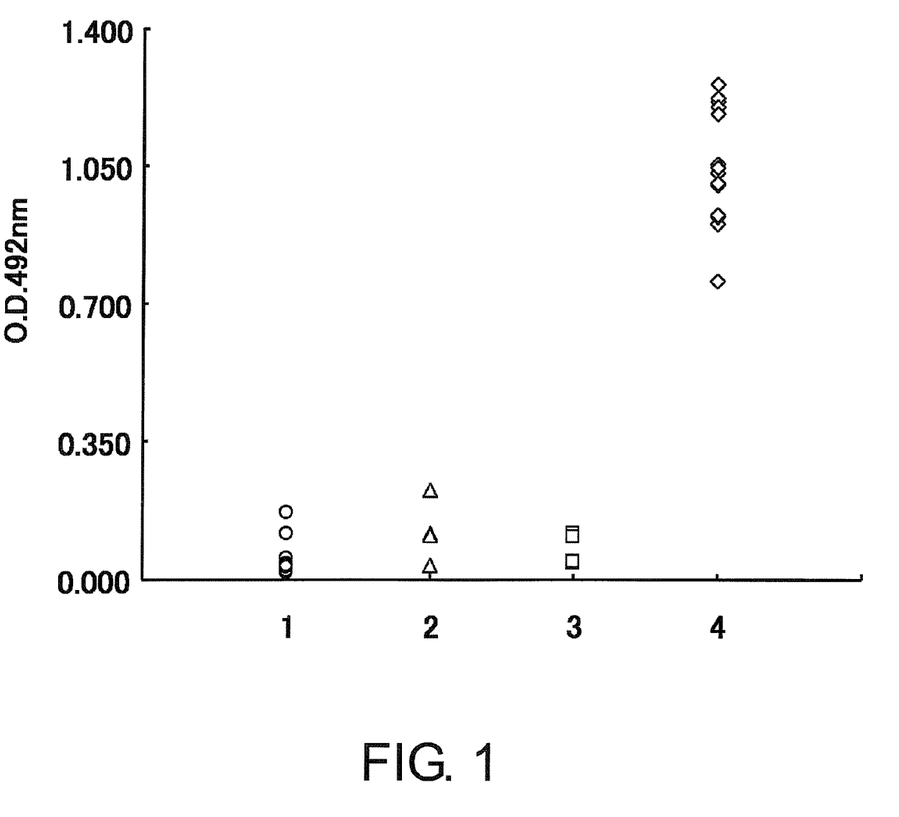
FIG. 1 shows the specificity of the reaction of FIV-vaccinated cat serum against cellular components. The reactivity of serum obtained from vaccinated SPF cats against FeT-J cell-derived cellular components was determined by ELISA. On the horizontal axis, 1 indicates the feline 3-way (feline panleukopenia virus, feline calicivirus, and feline infectious rhinotracheitis virus)-vaccinated group (open circle), 2 indicates the feline leukemia-vaccinated group (open triangle), 3 indicates the feline 3-way+feline leukemia-vaccinated group (open square), and 4 indicates the FIV-vaccinated group (open diamond).

In the FIV-vaccinated group, a strong reaction was observed to the cellular components. On the other hand, in the feline 3-way-vaccinated group, the feline leukemia-vaccinated group, and the feline 3-way+feline leukemia-vaccinated group, some had slightly reacted to the cellular components, but in all groups, the reactivity to the cellular components was clearly lower than that of the FIV-vaccinated group (FIG. 1).

Therefore, reactivity of serum to such cellular components was shown to be specific to cats vaccinated with the FIV vaccine.

Example 3

Comparison of Reactivity Depending on the Cell Line

[Materials and Methods]

FeT-J cells and 3201 cells which are feline lymphocyte-derived cell lines, CRFK cells which is a feline kidney-derived cell line, fcwf-4 cells which is a feline fetus-derived cell line, and Vero cells which is an African green monkey kidney-derived cell line were used. The respective cells were cultured, and solubilization and formalin treatment were carried out as described in Example 1 to prepare antigens for ELISA.

The sera from 27 SPF cats vaccinated three times with the FIV vaccine at three-week intervals (FIV-vaccinated group) and the sera from eight SPF cats infected with FIV (FIV-infected group) were used as samples.

ELISA was performed as in Example 2, and differences of the respective cells in their reactivity to the cellular components were determined.

[Results and Discussion]

Figure 2:
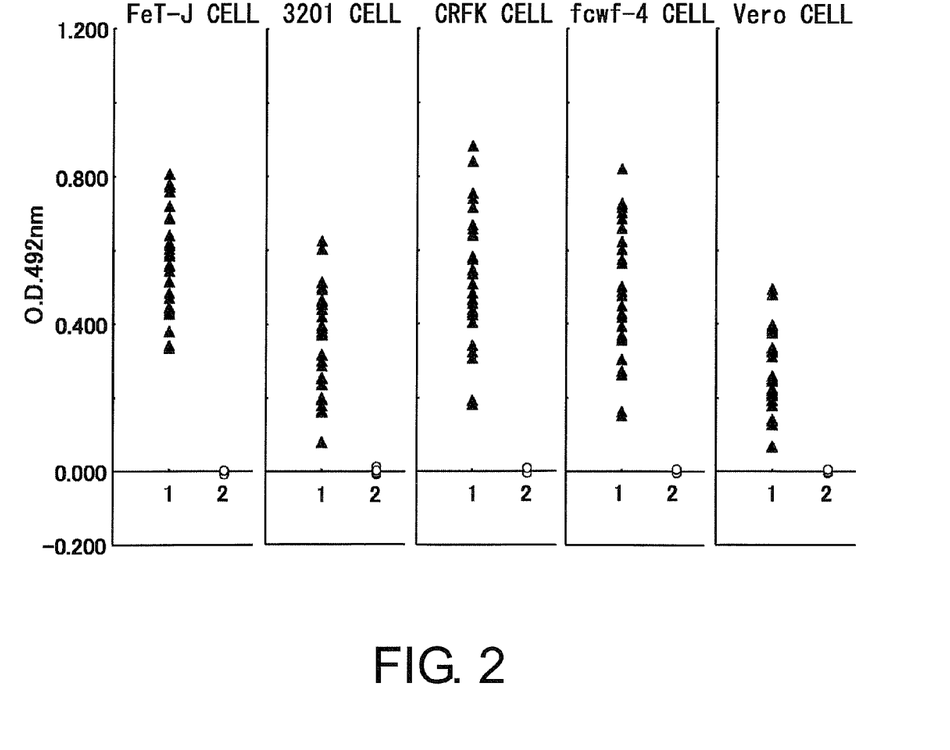
FIG. 2 shows the comparison of reactivities among cell lines. The reactivities of sera obtained from SPF cats vaccinated with an FIV vaccine and sera obtained from SPF cats experimentally infected with FIV to cellular components derived from cells from various tissues of cat and simian kidney cells were determined by ELISA. On the horizontal axis, 1 and 2 indicate the FIV-vaccinated group (filled triangle) and the FIV-infected group (open circle), respectively.

The sera from the FIV-vaccinated group highly reacted to the cellular components of all of the feline-derived cell lines. In addition, they highly reacted to cellular components of simian-derived Vero cells. On the other hand, the sera from FIV-infected cats did not react to the cellular components of any of the cell lines (FIG. 2).

Therefore, when measuring the reactivity of feline serum to cellular components for the purpose of confirming whether a cat is vaccinated with the FIV vaccine, cells used to prepare the cellular components which will serve as the diagnostic antigens were found not to be limited to specific cell lines or animal species from which they are derived.

Example 4

Each of the Cellular Constituents to Which a Serum of an FIV-Vaccinated Cat Reacts

[Materials and Methods]

FeT-J cells were fractioned into cytoplasm, cell membrane, cell nucleus, and cytoskeleton using a commercially available cell fractionation kit (Calbiochem, Subcellular ProteoExtract Kit). Each fraction was subjected to formalin treatment as described in Example 1 to prepare the antigens for ELISA. The antigens for ELISA of the respective fractions were diluted with a coating buffer so that the amount of protein was 200 ng/well, and were coated onto a 96-well ELISA plate.

The sera from three SPF cats vaccinated three times with the FIV vaccine at three-week intervals were used. The sera from one SPF cat infected with FIV and one SPF cat vaccinated with the feline 3-way vaccine were used as control.

ELISA was performed as described in Example 2.

[Results and Discussion]

The sera from FIV-vaccinated cats reacted with all cell fractions, and showed a strong reaction particularly with the cell membrane and cytoskeleton. On the other hand, the sera from FIV-infected cats did not react with any of the cell fractions, and the sera from cats vaccinated with the feline 3-way vaccine showed only a very weak reaction (Table 2).

TABLE 2

| FRACTION | FIV VACCINATED GROUP | | | CONTROL GROUP | |
|---|---|---|---|---|---|
| | ALI1 | ALG2 | ALP1 | ALF1[a] | C6[b] |
| CYTOPLASM | 0.732[c] | 0.673 | 0.789 | 0.053 | 0.131 |
| CELL MEMBRANE | 1.089 | 0.900 | 1.077 | 0.045 | 0.080 |
| CELL NUCLEUS | 0.552 | 0.475 | 0.596 | 0.036 | 0.057 |
| CELL CYTOSKELETON | 1.084 | 0.884 | 1.100 | 0.053 | 0.138 |

[a]FIV-infected cats
[b]Cats vaccinated with the feline 3-way vaccine
[c]Mean O.D. value (492 nm) of two wells Therefore, when measuring reactivity with feline serum using a certain fraction of the cellular constituents, the cellular constituent may be any of cytoplasm, cell membrane, cell nucleus, and cytoskeleton, and a high reaction was shown to be obtainable by using cell membrane and cytoskeleton in particular.

Example 5

Distinguishing FIV-Vaccinated Cats from FIV-Infected Cats by Dot Blot Method

[Materials and Methods]

FeT-J cells were suspended in PBS⁻ so that the cell count was approximately $2.0 \times 10^8$/mL, and sonicated for ten minutes using an output of 200 W to disrupt the cells. This was treated with formalin as described in Example 1, and the supernatant obtained by centrifugation at 20,000×g for ten minutes was filtered through a 0.2-μm filter to prepare FeT-J cellular component antigens.

The immunodominant region of the transmembrane protein which is a structural protein of FIV is reported to be useful for serological diagnosis of FIV infection (Fontenot, J. D., Hoover, E. A., Elder, J. H., Montelaro, R. C., 1992. Evaluation of feline immunodeficiency virus and feline leukemia virus transmembrane peptides for serological diagnosis. J. Clin. Microbiol. 30, 1885-1890). A synthetic peptide of the 14 amino acid residues (MQELGCNQNQFFCK; SEQ ID NO: 1) corresponding to this region was prepared as a Multiple Antigen Peptide (MAP), and used as a TM peptide antigen.

Serum from SPF cats three weeks after vaccination with the FIV vaccine three times at three-week intervals, serum from SPF cats experimentally infected with FIV, and serum from untreated SPF cats were used as samples.

FeT-J cellular component antigens and the TM peptide antigen were individually two-fold diluted serially with a TBS buffer, and they were adsorbed onto a nitrocellulose membrane using a dot blotting apparatus (Bio-Rad). The nitrocellulose membrane was soaked in 5% skim milk, and blocked by incubating it overnight at 4° C. The nitrocellulose membrane was soaked in each serum samples in 1:100 dilutions in a serum diluent, and this was reacted at room temperature for one hour. After washing the nitrocellulose membrane, this was incubated in an optimal dilution of POD-labeled anti-feline IgG goat serum in the serum diluent for one hour. The nitrocellulose membrane was washed and then soaked in a substrate solution for color development.

[Results and Discussion]

Figure 3:
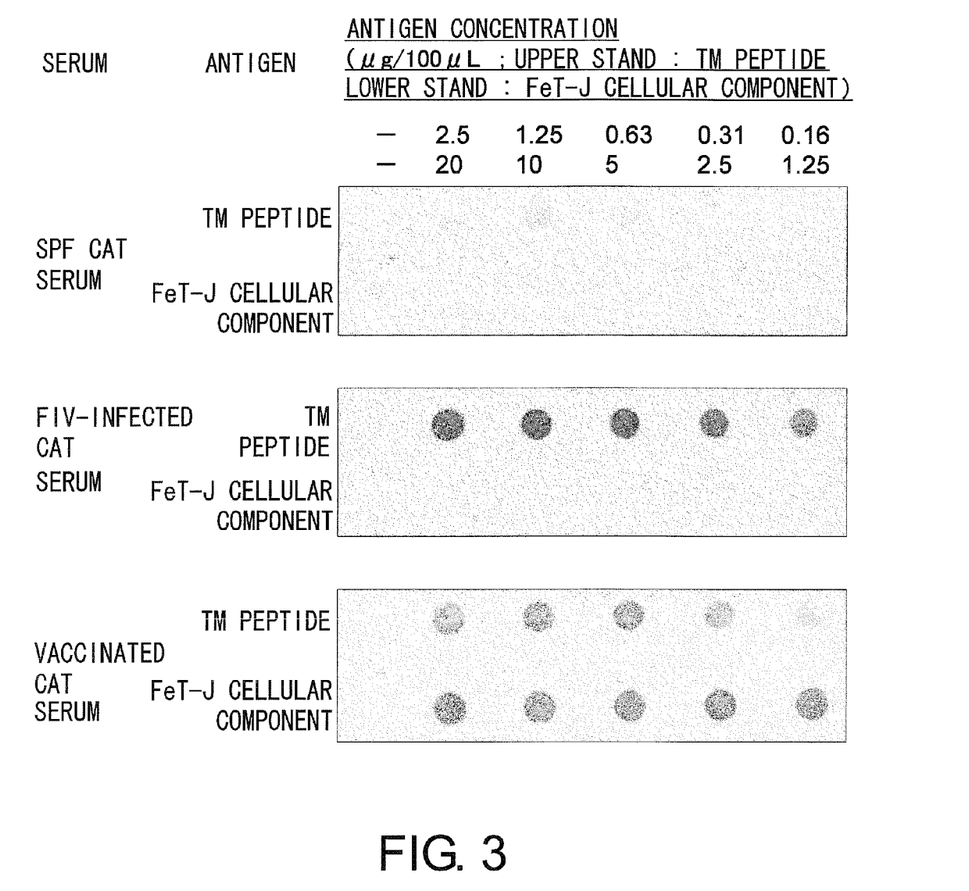
FIG. 3 depicts photographs showing the results of distinguishing FIV-vaccinated cats from FIV-infected cats by dot blot method. The reactivity of serum obtained from an SPF cat vaccinated with the FIV vaccine, serum obtained from an SPF cat experimentally infected with FIV, and serum obtained from an SPF cat to FeT-J cellular component antigens and the TM peptide antigen were examined by dot blot method.

The FIV-vaccinated cat serum reacted with both the TM peptide antigen and the FeT-J cellular component antigens. On the other hand, the FIV-infected cat serum showed strong reaction to the TM peptide antigen, but did not react to FeT-J cellular component antigens. Furthermore, SPF cat serum did not react to either of the antigens (FIG. 3).

Therefore, the use of dot blot method also showed that FIV-vaccinated cats and FIV-infected cats can be differentiated by investigating the reactivity of sera to cellular components.

Example 6

Detection of FIV-Vaccinated Cats by the Immunochromatography Method

[Materials and Methods]

To 1 mL of 40-nm particle size colloidal gold solution, 1 μL of 0.1 M potassium carbonate was added to adjust the pH to 8.0, and after further adding 40 μL of 0.5 mg/mL anti-feline IgG goat serum. After stirring the solution, this was incubated at room temperature for one hour. Next, 100 μL of 2 mM Borax solution supplemented with 10% BSA was added and stirred, and then this was incubated at room temperature for one hour. The supernatant was removed by centrifugation at 15,000 rpm for ten minutes, and the precipitate was resuspended in 1 mL of labeled antibody storage solution (1% BSA, 0.15 M NaCl, 0.1% $NaN_3$, 10 mM Tris-HCl, pH8.0). This was centrifuged again at 15,000 rpm for ten minutes, the supernatant was removed, and the precipitate was resuspended in 0.25 mL of labeled antibody storage solution to prepare the colloidal gold-labeled anti-feline IgG antibodies.

As antigens for the positive line, FeT-J cellular component antigens prepared in Example 5 were used. As antigens for the control line, anti-goat IgG rabbit serum was used. Each of the antigens were prepared at a protein level of 1.5 mg/mL, then applied to a nitrocellulose membrane, air dried, and then this was cut into few millimeter-wide strips for use.

Serum from SPF cats three weeks after vaccination with the FIV vaccine three times at three-week intervals, serum from SPF cats experimentally infected with FIV, and serum from untreated SPF cats were used as samples.

8 μL of feline serum, 8 μL of $PBS^-$, and 8 μL of developing solution ($PBS^-$ supplemented with 3% Tween20) were mixed in a microwell, and the tip of the strip was soaked in this mixed solution. Five minutes later, the strip was washed, and then dried at 37° C. for 30 minutes. 16 μL of colloidal gold-labeled anti-feline IgG antibody and 8 μL of developing solution were mixed in a microwell, and the tip of the dried strip was soaked in this mixed solution. Five minutes later, the presence or absence of each line was observed.

[Results and Discussion]

Figure 4:
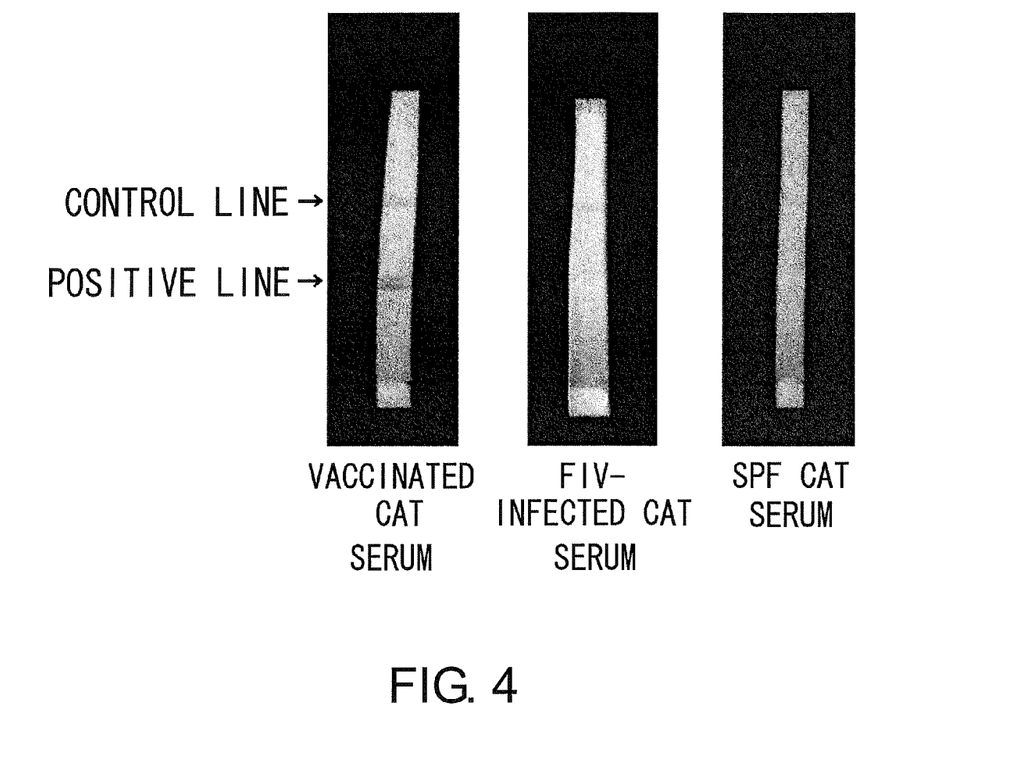
FIG. 4 depicts photographs showing the results of detecting an FIV-vaccinated cat by immunochromatography method. The reactivity of serum obtained from an SPF cat vaccinated with an FIV vaccine, serum obtained from an SPF cat experimentally infected with FIV, and serum obtained from an SPF cat to the FeT-J cellular component antigens and colloidal gold-labeled anti-feline IgG were determined by immunochromatography method.

Positive and control lines were observed in the FIV-vaccinated cat sera. On the other hand, the control line alone was confirmed in the FIV-infected cat sera and SPF cat sera (FIG. 4).

Therefore, this showed that the diagnostic method to distinguish vaccinated cats using cellular components can also be applied to immunochroatography method generally used as a simple diagnostic method.

INDUSTRIAL APPLICABILITY

Until now, FIV infection was diagnosed using antibody tests. Simple diagnostic kits that can be clinically used are now commercially available, and tests are performed exclusively in hospitals. However, after FIV vaccines were launched, vaccinated cats were also determined to be positive with these kits; therefore, diagnosis to distinguish vaccinated cats from infected cats required PCR tests done by testing institutions. This problem was discouraging veterinarians from vaccination.

Studies by the present inventors elucidated that antibodies against cellular components of cultured cells used to propagate FIV are produced in FIV-vaccinated cats. Reactivity to these cellular components is specific to FIV-vaccinated cats, and such antigens are useful as antigens for serologically distinguishing vaccinated cats from infected cats.

The test methods of the present invention using the above-mentioned antigens have enabled FIV-infected cats and FIV-vaccinated cats to be efficiently distinguished among anti-FIV antibody-positive cats by serological test methods.

The invention claimed is:

1. A method for testing the presence or absence of a feline immunodeficiency virus (FIV) vaccination history in a cat, the method comprising detecting an antibody against a non-FIV-derived cellular component in a test sample from the cat using an antigen-antibody reaction, wherein the antibody is produced as a result of vaccination with an FIV vaccine but not as a result of FIV infection and the cat is determined to have an FIV vaccination history when the antibody is detected.

2. The test method of claim 1, wherein the non-FIV-derived cellular component is a cell membrane, cytoplasm, nucleus, or cytoskeleton of an FIV-infected cell utilized to produce the FIV vaccine.

3. The test method of claim 1, wherein the non-FIV-derived cellular component is a cellular component of a feline-derived cell.

4. The test method of claim 1, wherein the non-FIV-derived cellular component is a cellular component of a cell derived from a non-feline animal.

5. The test method of claim 1, wherein serum, plasma, or whole blood derived from the cat is used as the test sample.

6. The test method of claim 2, wherein the non-FIV-derived cellular component is a cellular component of a feline-derived cell.

7. The test method of claim 2, wherein the non-FIV-derived cellular component is a cellular component of a cell derived from a non-feline animal.

8. The test method of claim 2, wherein serum, plasma, or whole blood derived from the cat is used as the test sample.

9. The test method of claim 3, wherein serum, plasma, or whole blood derived from the cat is used as the test sample.

10. The test method of claim 4, wherein serum, plasma, or whole blood derived from the cat is used as the test sample.

* * * * *

UNITED STATES PATENT AND TRADEMARK OFFICE
CERTIFICATE OF CORRECTION

PATENT NO.         : 8,394,581 B2
APPLICATION NO.    : 12/670592
DATED              : March 12, 2013
INVENTOR(S)        : Tsutomo Hohdatsu et al.

It is certified that error appears in the above-identified patent and that said Letters Patent is hereby corrected as shown below:

On the Title Page:

Item (73) the Assignee should read as follows:

(73)  Assignee:  Kitasato Daiichi Sankyo Vaccine Co., Ltd. (JP)

Signed and Sealed this
Ninth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO.       : 8,394,581 B2                                                        Page 1 of 1
APPLICATION NO. : 12/670592
DATED            : March 12, 2013
INVENTOR(S)      : Hohdatsu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 228 days.

Signed and Sealed this

First Day of September, 2015

Michelle K. Lee
*Director of the United States Patent and Trademark Office*

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial
<220> FEATURE:
<223> OTHER INFORMATION: An artificially synthesized peptide sequence

<400> SEQUENCE: 1

Met Gln Glu Leu Gly Cys Asn Gln Asn Gln Phe Phe Cys Lys
1               5                   10
```